(12) United States Patent
Dorn et al.

(10) Patent No.: US 9,687,372 B2
(45) Date of Patent: Jun. 27, 2017

(54) HAND UNIT TO RELEASE A SELF-EXPANDING IMPLANT

(71) Applicant: C. R. Bard, Inc., Murray Hill, NJ (US)

(72) Inventors: Jurgen Dorn, Neulussheim (DE); Martina Hoffman, Stutensee (DE)

(73) Assignee: C.R. Bard, Inc., Murrary Hill, NJ (US)

( * ) Notice: Subject to any disclaimer, the term of this patent is extended or adjusted under 35 U.S.C. 154(b) by 164 days.

(21) Appl. No.: 14/056,843

(22) Filed: Oct. 17, 2013

(65) Prior Publication Data

US 2014/0107757 A1    Apr. 17, 2014

Related U.S. Application Data

(60) Provisional application No. 61/715,178, filed on Oct. 17, 2012.

(51) Int. Cl.
*A61F 2/966* (2013.01)
*A61F 2/95* (2013.01)

(52) U.S. Cl.
CPC ...... *A61F 2/966* (2013.01); *A61F 2002/9517* (2013.01); *F04C 2270/0421* (2013.01)

(58) Field of Classification Search
CPC ..... A61F 2002/9517; A61F 2/95; A61F 2/966
See application file for complete search history.

(56) References Cited

U.S. PATENT DOCUMENTS

| | | | |
|---|---|---|---|
| 4,846,793 A | | 7/1989 | Leonard et al. |
| 5,433,723 A | * | 7/1995 | Lindenberg et al. ......... 606/198 |
| 5,571,168 A | * | 11/1996 | Toro .............................. 623/1.11 |
| 6,551,333 B2 | | 4/2003 | Kuhns et al. |
| 7,326,236 B2 | | 2/2008 | Andreas et al. |
| 8,075,607 B2 | | 12/2011 | Melsheimer |
| 2007/0244540 A1 | | 10/2007 | Pryor |
| 2009/0192518 A1 | * | 7/2009 | Golden et al. ................ 606/108 |
| 2010/0274340 A1 | | 10/2010 | Hartley et al. |
| 2010/0318092 A1 | | 12/2010 | Butler et al. |
| 2011/0046710 A1 | * | 2/2011 | Mangiardi et al. .......... 623/1.11 |
| 2011/0295354 A1 | | 12/2011 | Bueche et al. |
| 2012/0238806 A1 | | 9/2012 | Mangiardi et al. |

OTHER PUBLICATIONS

PCT/EP2013/071712 filed Oct. 17, 2013 International Search Report and Written Opinion dated Dec. 6, 2013.

* cited by examiner

*Primary Examiner* — Thomas McEvoy
(74) *Attorney, Agent, or Firm* — C.R. Bard Intellectual Property

(57) ABSTRACT

An elongate hand unit for deploying an elongate implant from the distal end of a delivery catheter. The hand unit has a distal end and a proximal end separated by a hand unit length. The hand unit may include a pull component and a push component. The pull component may include a pull grip sliding on the push component to deploy the implant. The push component may be operatively connected to the push element and include at its proximal end a push surface to receive during deployment of the implant a force that pushes on the push element shaft to resist proximal movement of the implant during deployment. The push component may provide a guide rail that defines a guide path for the pull grip, whereby proximal movement of the pull grip along the guide path deploys the implant.

15 Claims, 2 Drawing Sheets

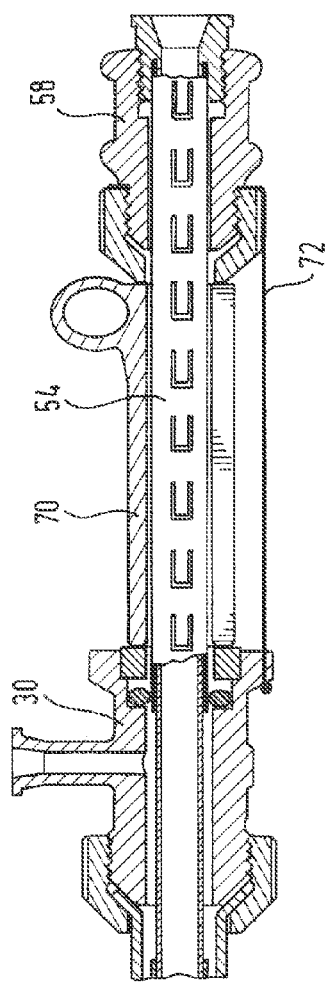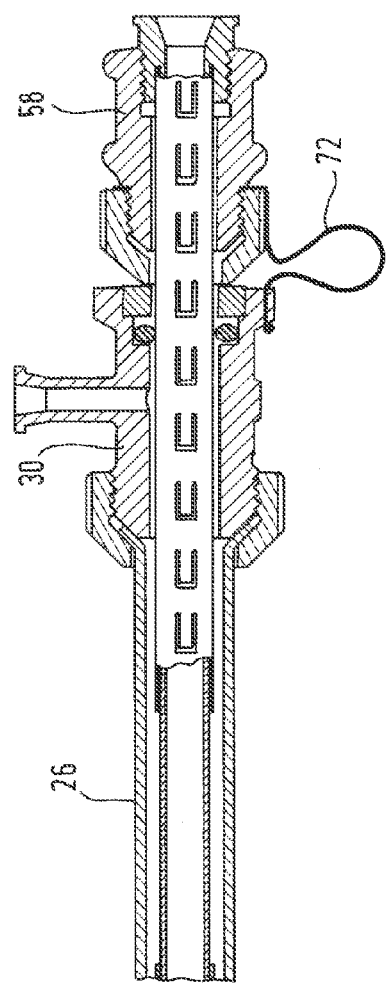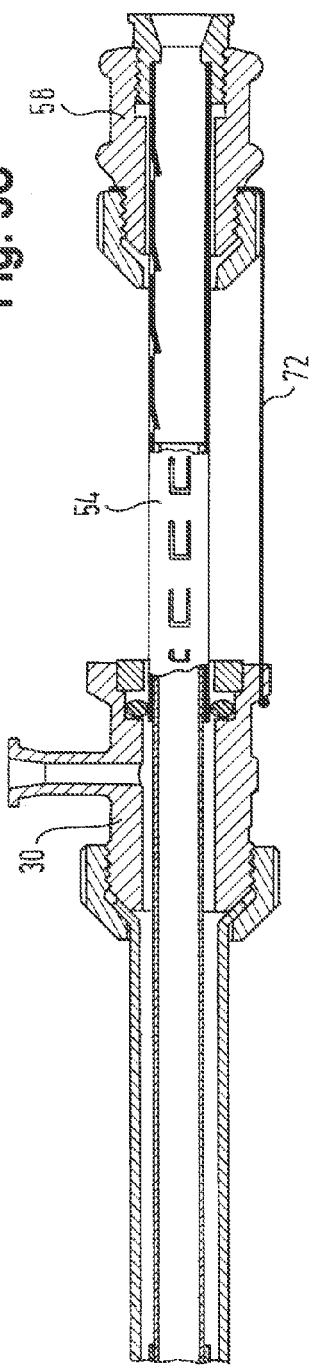

HAND UNIT TO RELEASE A SELF-EXPANDING IMPLANT

PRIORITY

This application claims the benefit of U.S. Provisional Application No. 61/715,178, filed Oct. 17, 2012, and of NL Application No. N2009648, filed Oct. 17, 2012, each of which is incorporated by reference in its entirety into this application.

TECHNICAL FIELD

This invention relates to a hand unit for a catheter device for the delivery of an elongate implant mounted on the distal end of the device.

More particularly, this invention relates to an elongate hand unit for deploying an elongate implant from the distal end of a delivery catheter, which catheter has a shaft between the distal end carrying the implant and a proximal end to which the hand unit may be coupled, the shaft comprising a push element to maintain the position of the implant during deployment and a pull element to be pulled proximally relative to the push element, by a release distance sufficient to deploy the implant, the hand unit having a distal end and a proximal end separated by a hand unit length, and comprising a pull component and a push component, the pull component having a pull grip, to be gripped and pulled proximally by the release distance, sliding on the push component, thereby to pull the pull element proximally, thereby to deploy the implant, the push component to be operatively connected to the push element of the catheter shaft and having at its proximal end a push surface to receive during deployment of the implant a force that pushes on the push element shaft to resist proximal movement of the implant during deployment, the push component providing a guide rail that defines a guide path for the pull grip, with a guide path length along which the pull grip can slide proximally, from a distal to a proximal end of the guide rail whereby the proximal movement of the pull grip along the guide path deploys the implant.

BACKGROUND

Catheter delivery systems for trans-luminal delivery of implants, particularly self-expanding stents, have a rich history in the patent literature. Early proposals were for a simple sheath radially surrounding the radially-compressed stent at the distal end of the catheter system, the sheath being pulled back proximally, to release the stent from its bed, progressively, starting at its distal end of the bed, within the stenting site or stenosis of the bodily lumen in which the catheter delivery system had been advanced. Readers will appreciate that, because the stent is self-expanding, it is pressing on the luminal surface of the surrounding sheath, up to the moment of its release from the sheath. Thus, friction forces between the stent and the surrounding sheath must be taken into account when devising a delivery system that will allow the sheath to slide proximally over the full length of the outwardly-pushing, self-expanding stent.

The problems of friction will increase with the length of the stent, and the pressure on delivery system designers is to deliver ever-longer stents. Furthermore, there is steady pressure on stent delivery system designers to come up with systems that have ever-smaller passing diameters at the distal end of the catheter. The conventional unit of dimensions for diameters of systems to advance along a bodily lumen is the "French" which is one third of a millimeter. Thus, one millimeter is "3 French". To be able to reduce the passing diameter of a delivery system, for example from 7 French to 6 French, is a notable achievement.

One way to respond to the challenge of friction forces between a proximally withdrawing sheath and a self-expanding stent confined within it is to adopt a "rolling membrane" sheath system, in which the sheath is at least double the length of the stent that it surrounds, being doubled back on itself at a point distally beyond the distal end of the stent. Then, proximal withdrawal of the radially outer doubled back portion of the sheath length will cause the "rolling edge" between the outer and inner sheath portions to retreat proximally, rolling proximally down the length of the stent, to release the stent progressively, as with a single layer surrounding sheath.

Regardless of whether a conventional or rolling membrane sheath system is employed at the distal end of a stent delivery system, the delivery system requires some form of deployment mechanism provided at the proximal end of the stent delivery system to enable an operator to control at the proximal end the deployment of the distally located stent inside a patient. Typically, the stent is provided on the distal end of a push rod that extends from the proximal end to the distal end of the system. With this push rod held stationary, the user operates such a mechanism at the proximal end, resulting in the sheath system being pulled back, thereby deploying the stent, as described above.

One stent deployment mechanism is disclosed in U.S. 2007/0244540 A1 (here "D1"), which is incorporated by reference in its entirety into this application. This mechanism involves the use of a thumb slider that is repeatedly translated distally and proximally, with each progressive proximal movement effecting progressive retraction of the sheath. A disadvantage of this deployment mechanism is the inability to deploy the stent in only one, or at least only a few, translations of the deployment mechanism. For lengthy stents, deploying the stent using this mechanism would prove a laborious task, requiring many translations. However, once the distal end of the implant is in place on the wall of the lumen in the body that is receiving the implant, a swift retraction of the sheath, to deploy the remaining length of the implant in one smooth stroke, is not available from this device.

D1 teaches the attractiveness of a hand unit that is physically small. The sheath of D1 is not a roll back membrane. Were it to be a roll back membrane, the distance it would have to be pulled back proximally would be doubled. The present invention aims to provide a simple and easy to manufacture hand unit that is small in size but yet is capable of deploying a lengthy implant covered by a roll back membrane.

SUMMARY

According to the present invention, a hand unit of the general form identified above is characterized by a guide path extender that is movable from a compact disposition in which the push surface is a first distance from the distal end of the hand unit to an extended disposition in which the push surface is a second distance, greater than the first distance, from the distal end of the hand unit, the guide path extender making available to the pull grip an increased guide path length.

With the invention, the guide path extender provides a guide path length that is long enough to pull back proximally the pull element of the catheter shaft, far enough to deploy a lengthy implant at the distal end of the catheter, even if the implant is constrained by a roll back membrane that needs to be pulled back proximally by a distance double the length of the implant itself.

Furthermore, the invention makes available a system to deploy an implant in which the pull grip travels over a linear path that is co-linear with the longitudinal axis of the implant. Providing such a path can maximise the tactile feedback that the operator obtains from the distal end of the implant delivery stem via the pull grip. Not only that; the transmission of deployment force from the pull grip to the membrane that radially restrains the implant till it is deployed is achieved most efficiently through a line of action that is as straight as possible and a minimum of end-to-end joints in the line of force transmission.

The state of the art includes proposals to release a self-expanding stent from a delivery catheter with a hand unit that includes a reel on which a pull wire can be wound, the winding of the pull wire on the reel serving to pull back proximally a sheath surrounding the implant at the distal end of the catheter. Conveniently, successive squeezes of a trigger can be used to achieve successive stepwise rotary movement of the reel, each squeeze of the trigger pulling back proximally the sheet surrounding the implant, by a step along the length of the implant. However, complexity is added by the need to convert the sheath surrounding the implant into a pull wire for winding up on the reel. Furthermore, some doctors prefer to deploy an implant in one smooth single proximal movement of a pull grip, and so are less comfortable with deployment using a large number of successive squeezes of a trigger. In principle, a single long stroke of the pull grip, to deploy the implant, is preferable whenever a more rigorously stepwise deployment procedure runs a risk of imposing on the bodily tissue of the lumen while receiving the implant any sort of axial stress along the length of the bodily lumen. The chances of such stresses being imposed on the tissue during a single full stroke release of the implant are likely to be significantly less. Minimising tissue trauma during implant deployment is of course a general aim in all implant deployment procedures and the present invention can help to minimise such trauma.

Thus, a technical effect of the present invention is to minimise tissue trauma when deploying self-expanding implants of more than average length.

One way to provide the extra guide rail length is to resort to a push component in the hand unit that is of the form of a telescopic tube arrangement. Effectively, the guide path extender extends distally of the guide path. Such an arrangement is likely to exhibit first and second telescopically arranged tubes, one radially inside the other and with a latch between them that permits the tubes to extend their length telescopically but which resists the reverse movement, to a smaller length. This is because the push surface is on the proximal end of the push element, and any tendency for the length of the telescopic tube arrangement to collapse could frustrate delivery of a pushing force to the distal end of the catheter where it is required to keep the implant in position during deployment. Such a latch can be very simply and economically provided by a series of detents, tangs or tabs on one of the tubes, that will abut an end surface on the other of the tubes to resist any telescopic collapsing relative movement between the two tubes. With a telescopic arrangement, the guide rail can be provided exclusively on the radially outer of the telescoping tubes, with no requirement for any guide rail surface on the radially inner of the two tubes. One example of such an arrangement can be seen in the accompanying drawings, described below. It may be convenient to arrange that the passage of each detent past the end of the other of the telescopic tubes results in an audible clicking sound, to inform the operator that the latch has engaged.

Other than a telescopic arrangement, the push component can be provided as first and second guide rail portions (and optionally more guide rail portions), e.g. in the form of rods or tubes, that can couple together, co-linearly and, in the case of tubes, co-axially, to deliver together a guide rail and aggregate guide path length that is greater than that present on any of the guide rail portions individually. One can regard this as providing the guide path extender proximal of the guide path as such. Just as a chimney sweep can screw together endwise tube sections to advance a sweeping brush up a chimney, or a person unblocking drains can screw together endwise a series of rods that will be advanced along the length of a drain, so the implant deployer can take at least first and second push component rods or tubes and join them together endwise to provide a run of guide rail that is long enough to accommodate the full length of pull element of the implant delivery catheter that needs to be accommodated within the hand unit to release the implant from the distal end of the catheter. Of course, endwise assembly of second and further push component rods or tubes increases the length of the hand unit. However, the need for a short and compact hand unit is felt during assembly, packaging and transport of the delivery system. During deployment of the implant, a much greater length of the hand unit can be tolerated, temporarily.

In another variant, reminiscent of a collapsible walking stick, the guide rail can be provided in portions linked end-to-end by elastic bands that allow the portions to be stowed side by side but which, on release, bring the portions into an end-to-end connected relationship to provide one long guide rail that is cylindrical with no irregularities on the continuous guide path surface.

As to the push component of the hand unit, it will generally be convenient to provide the push surface on a push hub at the proximal end of the hand unit. That hub would conveniently receive a guidewire, in the case that the delivery catheter is an "over the wire" device. Otherwise, the push hub will conveniently include a coupling for a flushing line to deliver flushing liquid to flush the interior of the delivery catheter of gas prior to advancing the catheter into the bodily lumen that is to receive the catheter.

Likewise, the pull grip can be provided in the form of a pull hub that slides on the guide rail and that pull hub can conveniently include a coupling for flushing liquid.

In general, devices that are to be actuated often include one or other safety device that prevents premature actuation, and might require a "cocking" or "priming" action as a first step in the actuation process. So it can be with the hand units of the present invention. In particular, it can be useful to include a spacer that sets a minimum distance between the push surface and the pull grip, which spacer is removed prior to actuating the device. In particular embodiments, there may be advantage in having a device such as a tether that will set a maximum distance that separates the push surface and the pull grip. Such a device is illustrated in the accompanying drawings.

The hand unit of the present invention will serve as part of an implant delivery catheter system. In one simple arrangement, the push element of the catheter has a proximal end portion that extends proximally into the hand unit and provides the said push component. In a delivery system that utilises a rolling membrane to deploy a self-expanding implant at the distal end of the system, the membrane can be extended back proximally, all the way to the pull component of the hand unit.

BRIEF DESCRIPTION OF THE DRAWINGS

For a better understanding of the present invention, and to show more clearly how the same may be carried into effect, reference will now be made, by way of example, to the accompanying drawings, in which

FIG. 3A shows the hand unit of FIG. 1, in the same axial section, in a transport disposition, prior to actuation;

FIG. 3B is the same section as FIG. 3A, but after a first step in the stent deployment process; and FIG. 3C is the same section as FIGS. 3A and 3B, but showing the hand unit after a further step in the deployment process.

DETAILED DESCRIPTION

Figure 1:
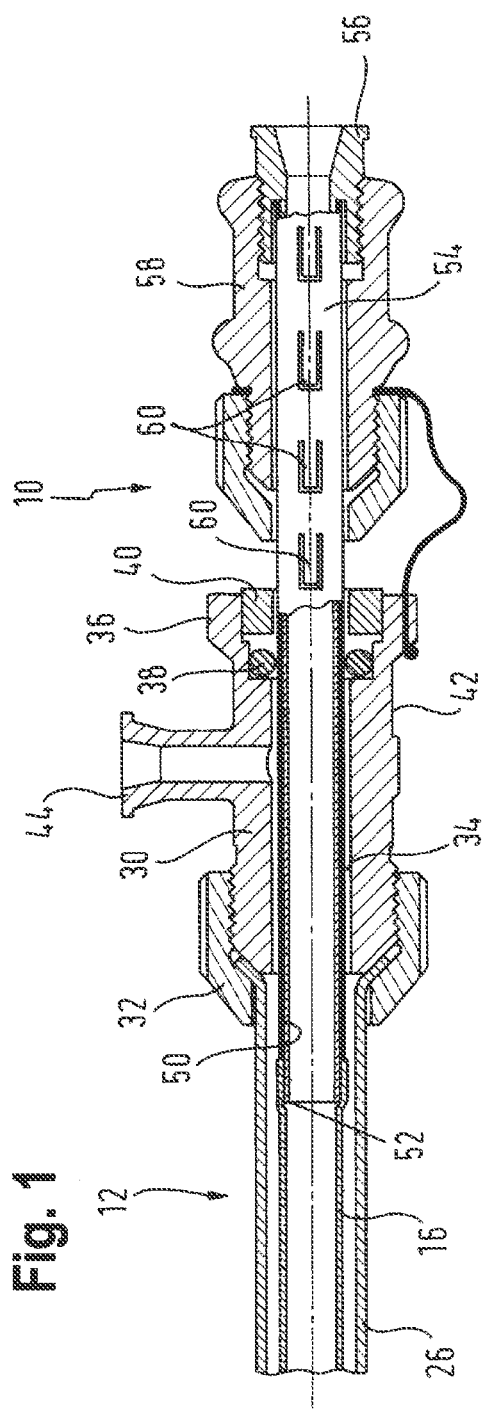
FIG. 1 is a section through the long axis of a hand unit in accordance with the present invention.
Figure 2:
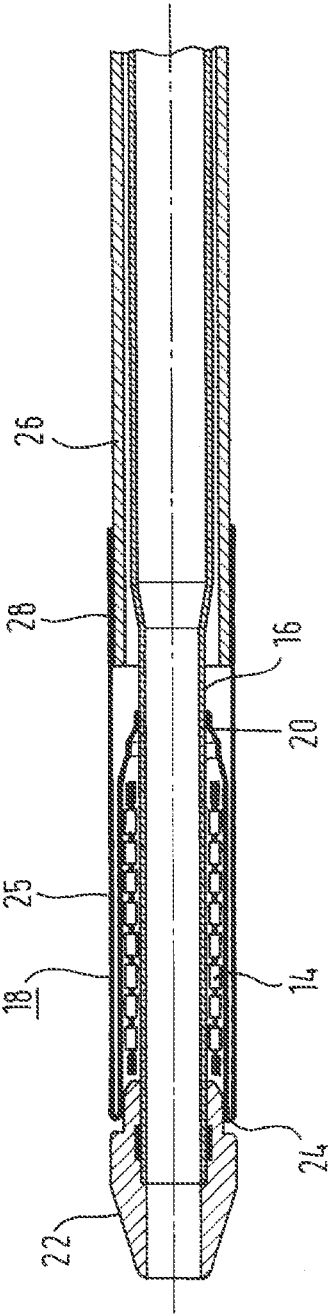
FIG. 2 is a section through the long axis of the distal end of a stent delivery catheter that has at its proximal end the hand unit of FIG. 1.

FIG. 1 shows a hand unit 10, coupled to the shaft 12 of a catheter delivery system for the stent 14 shown in FIG. 2. The catheter shaft 12 has an inner shaft 16 which is the push element of the catheter shaft. As can be seen from FIG. 2, the stent 14 is carried on the distal end of the inner shaft 16 and is radially confined by a roll back membrane 18 with a distal end 20 secured to the inner shaft 16 at a location just proximal of the proximal end of the stent 14. The membrane extends distally to the tip 22 of the catheter, at which point it reverses direction at a roll back annulus 24 and then advances proximally in a proximal overlapping run 25 down the length of the stent. A little way proximal of the stent, the membrane 18 is bonded to a catheter outer shaft component 26, in an overlap zone 28 at the distal end of the outer shaft 26.

Following the outer shaft 26 back to its proximal end, we find it gripped between a pull hub 30 and a collar 32 threadably engaged with the pull hub. The pull hub has a bore 34 and a proximal end 36 which accommodates an O-ring 38 and retainer annulus 40. In the cylindrical outer surface 42 of the pull hub 30 there is provided a female Luer lock connection 44 to receive flushing liquid to flush the bore 34 defined by the pull hub 30.

Turning to the inner shaft 16 of the catheter, it terminates at its proximal end in a telescopic tube arrangement of the push component of the hand unit 10. The telescopic arrangement features an inner tube 50 with a distal end 52 that is received within the proximal end of the catheter inner shaft tube 16. Sleeving the inner tube 50 within its bore is the radially outer tube 54 of the telescopic arrangement. The outer telescope tube 54 runs back proximally as far as a female Luer connector 56 to receive flushing liquid to flush the bore of the catheter inner shaft tube 16. Around the Luer 56 is a push hub 58 so that one can push on the push hub 58 to push on the catheter shaft inner tube 16 and thereby hold the stent in position during its deployment. Collapsing of the telescopic arrangement is prevented by a series of tangs 60 that are each formed with a simple U-shaped cut through the wall thickness of the outer tube 54, each tang being predisposed to be inclined very slightly radially inwardly, thereby to bear on the proximal end of the inner tube 50 should any attempt be made to collapse the telescopic arrangement longitudinally. Pulling each tang 60 proximally past the proximal end of the inner tube 50 results in the issuance of an audible "click".

To illustrate how the hand unit of FIG. 1 is capable of deploying the stent 14, attention is now invited to FIGS. 3A, 3B and 3C of the drawings.

First, looking at FIG. 3A, we see an axial gap between the pull hub 30 and the push hub 58. The gap is preserved by a spacer 70 and a tether 72. The spacer 70 can be removed when the time comes to deploy the stent. It simply clips around the outer telescopic tube 54 and physically prevents the two hubs 30 and 58 from moving any closer together.

The two hubs cannot move further apart because the tether 72 that connects the two of them is taut. Unlike the spacer 70, the tether remains, connecting the two hubs, throughout the deployment process. The cylindrical radially outer surface of the outer telescopic tube 54 is smooth and provides a smooth, circular cross section guide rail along which the pull hub 30 can slide proximally, without impediment once the spacer 70 has been taken away.

Indeed, FIG. 3B shows that first step of the deployment process. Note that the push hub 58 has not moved but that the spacer 70 has been taken away and the pull hub 30 has been pulled back, by the distance of the spacer 70, until it lightly abuts the distal end of the push hub 58. This movement collapses the tether 72 and also pulls back proximally the outer catheter shaft 26 sufficient to pull back proximally the roll back annulus 24 to a point some distance proximal of the distal end of the stent 14, in the illustrated case about half way along the length of the stent 14.

The position shown in FIG. 3B is only transient. The next step is to pull proximally (rather than push distally) the push hub 58, thereby to extend telescopically the telescopic arrangement of the push component 50/54. During this movement, the pull hub 30 does not move axially relative to the push element, the inner shaft 16 of the catheter, so there is no further deployment of the implant during the proximal withdrawal of guide rail 54.

With the movement of the push hub completed, proximal movement of the pull hub is once again possible until the tether 72 once again goes taut. Reverse movement of the guide rail is prevented by that one of the series of tangs 60 which is immediately proximal of the proximal end of the inner tube 50 but which is first to engage with the proximal end as soon as any push force is imposed on the push hub 58. After this proximal extension of the telescope guide rail arrangement, the pull hub 30 is once again free to embark on a run along the length of the guide rail surface of the outer telescope tube 54, in the proximal direction, thereby to carry the rolling annulus 24 along the length of the proximal half of the length of the stent 14, thereby to complete its release and deployment into the bodily lumen that has received the catheter delivery system.

It will apparent that there are many other ways in which to realise the present invention than the one shown in the drawings. One could, for example, provide a hand unit with the push hub on a separate tube component that is, prior to deployment, simply offered up to the proximal end of the push component of the hand unit, thereby to provide an increased length of the guide rail, considerably longer than the length of the hand unit without the extension tube.

In another embodiment, there could be more than one such extension tube (in the manner of walking sticks, chimney rods or drain rods). While the illustrated telescope arrangement has only two tubes, it is envisaged that longer telescopes, of three or more tubes, would also be feasible. While the tangs shown in the drawings are a reliable and economical latch, skilled readers will be readily able to envisage other sorts of latch to endow a telescopic arrangement with the capability to resist telescopic collapse in length.

Notably, the present invention lends itself to modular construction of delivery systems for implants, tailored to the particular length of the specific implant to be delivered. With increasing maturity of technology in the world of stenting, it becomes ever more important to provide systems that lend themselves to straightforward manufacturing, in which sterility issues can be well managed. Keeping system design simple is not only a way to keep manufacturing simple, but is also a way to minimise variability and uncertainty in the operating theatre. Generally, the simpler a delivery system is, mechanically, the more reliable it will be in performance and therefore the safer for patients and the more favoured by their medical practitioners.

What is claimed is:

1. A medical device comprising:
    an implant;
    a catheter including:
        an inner shaft configured as a push element; and
        an outer shaft configured as a pull element; and
    a hand unit comprising:
        a pull component coaxially disposed on the outer shaft;
        a pull grip coaxially disposed within the outer shaft, wherein a proximal end of the outer shaft is captured between the pull component and the pull grip;
        a telescopic tube arrangement comprising an inner tube and an outer tube, wherein a distal end of the inner tube is disposed within a proximal end of the inner shaft;
        a series of tangs cut through the outer tube and disposed radially inward to engage the proximal end of the inner tube; and
        a push component coaxially disposed on a proximal end of the outer tube comprising a push surface disposed coaxially on the push component, wherein the push component is proximal the pull grip and pull component.

2. The medical device of claim 1 wherein the telescopic tube arrangement provides a guide path extender for the pull grip.

3. The medical device of claim 2 wherein the telescopic tube arrangement further comprises a latch between the inner tube and the outer tube that permits the telescopic arrangement to increase in length but resists length reductions.

4. The medical device of claim 3 wherein the inner tube and the outer tube couple together to deliver an aggregate guide path length greater than that provided by each of the inner tube and outer tube alone.

5. The medical device of claim 3 wherein the push surface is on a push hub.

6. The medical device of claim 5 wherein the push hub can receive a guide wire.

7. The medical device of claim 5 wherein the push hub includes a coupling for a flushing liquid.

8. The medical device of claim 1 further comprising a flexible tether disposed between the push component and the pull grip.

9. The medical device of claim 8 wherein the pull grip is a pull hub.

10. The medical device of claim 8 further comprising a removable spacer that sets a minimum distance separating the push surface and the pull grip.

11. The medical device of claim 10 wherein the catheter includes a distally located rolling membrane that couples between the inner shaft and outer shaft.

12. The medical device of claim 1 further comprising a removable spacer that sets a minimum distance separating the push surface and the pull grip.

13. The medical device of claim 1 wherein the catheter includes a distally located rolling membrane that couples between the inner shaft and outer shaft.

14. The medical device of claim 1 wherein the telescopic tube arrangement further comprises a latch between the inner tube and the outer tube that permits the telescopic arrangement to increase in length but resists length reductions.

15. The medical device of claim 14 wherein the inner tube and the outer tube couple together to deliver an aggregate guide path length greater than that provided by each of the inner tube and outer tube alone.

* * * * *